US008028870B2

(12) United States Patent
Mashiko et al.

(10) Patent No.: US 8,028,870 B2
(45) Date of Patent: Oct. 4, 2011

(54) EYELESS SEWING NEEDLE AND FABRICATION METHOD FOR THE SAME

(75) Inventors: Masaki Mashiko, Tochigi (JP); Kanji Matsutani, Tochigi (JP); Kosuke Shinohara, Tochigi (JP); Mieko Akaba, Tochigi (JP)

(73) Assignee: MANI, Inc., Tochigi (JP)

( * ) Notice: Subject to any disclaimer, the term of this patent is extended or adjusted under 35 U.S.C. 154(b) by 516 days.

(21) Appl. No.: 12/280,662

(22) PCT Filed: Feb. 27, 2007

(86) PCT No.: PCT/JP2007/054137
§ 371 (c)(1),
(2), (4) Date: Sep. 17, 2008

(87) PCT Pub. No.: WO2007/100127
PCT Pub. Date: Sep. 7, 2007

(65) Prior Publication Data

US 2009/0039117 A1 Feb. 12, 2009

(30) Foreign Application Priority Data

Feb. 28, 2006 (JP) ................................ 2006-051499

(51) Int. Cl.
*D05B 85/06* (2006.01)
*A61B 17/06* (2006.01)

(52) U.S. Cl. ......................... 223/102; 112/224; 606/224

(58) Field of Classification Search .................. 223/102; 128/339; 606/223–226; 29/428
See application file for complete search history.

(56) References Cited

U.S. PATENT DOCUMENTS

| | | | | |
|---|---|---|---|---|
| 3,394,704 | A * | 7/1968 | Dery | 606/224 |
| 4,935,029 | A * | 6/1990 | Matsutani et al. | 606/223 |
| 5,012,066 | A | 4/1991 | Matsutani et al. | |
| 5,533,982 | A * | 7/1996 | Rizk et al. | 604/239 |
| 7,892,255 | B2 * | 2/2011 | Schaller et al. | 606/228 |
| 2004/0122472 | A1 | 6/2004 | Collier et al. | |
| 2006/0004389 | A1 * | 1/2006 | Nguyen et al. | 606/151 |

FOREIGN PATENT DOCUMENTS

| | | | |
|---|---|---|---|
| EP | 1481645 | A | 12/2004 |
| GB | 2113588 | A | 8/1983 |
| JP | 33090330 | A * | 4/1988 |
| JP | 64-011084 | A | 1/1989 |
| JP | 2-154746 | A | 6/1990 |

* cited by examiner

*Primary Examiner* — Ismael Izaguirre
(74) *Attorney, Agent, or Firm* — Smith Patent Office

(57) ABSTRACT

In an eyeless sewing needle, a periphery of an axial hole at the base end is heated to make a fibrous structure be a granular structure without directionality, and at least a part of a heat-affected zone made between the fibrous structure and the granular structure due to the heating is within a range that is three times the diameter of the sewing needle and that extends from an effective base of the axial hole towards the needle-point. This allows provision of a flexible sewing needle so that the hole periphery can be processed while keeping a hard state at the position of the needlepoint slightly away from the axial hole.

2 Claims, 3 Drawing Sheets

EYELESS SEWING NEEDLE AND FABRICATION METHOD FOR THE SAME

TECHNICAL FIELD

The present invention relates to an eyeless sewing needle and a fabrication method for the same. It particularly relates to an eyeless sewing needle made of austenitic stainless steel having a fibrous crystalline structure extending along the length of the sewing needle.

BACKGROUND ART

Stainless steel is a suitable material for sewing needles to be used in surgical operations. In the case of martensitic stainless steel, precipitation hardening stainless steel, or the like, wire rods each 6 to 10 mm in diameter are used as the material. In the case of carbon steel or martensitic stainless steel, wire drawing is carried out repeatedly thereto, providing wires each having the diameter of a sewing needle being fabricated. In the case of stainless steel, a solution heat treatment is carried out between each wire drawing.

These wires are cut at an appropriate length, and tips thereof are then sharpened by grinding using a grindstone into a cone or pyramid shape, which is then incurvated through machining and a hole passing through from a base end towards the tip side is made using a drill or a laser. Afterwards, the tip is mainly quenched, and a suture thread is inserted in the above-mentioned hole, and crimped and fixed. In the case of precipitation hardening stainless steel, once wire drawing and the solution heat treatment are carried out repeatedly until the thickness of the sewing needle is reached, it is cut at a predetermined length, the tip is sharpened as mentioned above, and then a hole is made in the base end. Afterwards, precipitation hardening other than quenching is carried out.

Since the above materials are soft, processing is easy, but there is a problem with quenching and precipitation hardening in that cracking, breaking, chipping, or the like easily occurs due to lack of toughness. Furthermore, there is a problem with corrosion resistance since rust easily develops due to characteristics of the materials.

With regard to these problems, Japanese Patent Publication after examination (Kokoku) No. Hei 1-11084 proposes a fabrication method for completing a product by using austenitic stainless steel wires extended at an 80% or greater cross-sectional area reduction rate, and in subsequent processing, carrying out predetermined processing on these steel wires while always maintaining at a temperature below approximately 500° C. Since hardness increased through work hardening, or strain hardening decreases when exceeding 500° C., the temperature is set to no greater than 500° C. While austenitic stainless steel cannot be quenched, work hardening at the time of wire drawing is utilized instead. Utilization of austenitic stainless steel allows improvement in corrosion resistance. Furthermore, since quenching is impossible, the problem of cracking or chipping does not occur by contrast.

The austenitic stainless steel extended to a predetermined diameter in this manner becomes a thin fibrous structure with crystal grains extending along the line length, providing the necessary hardness for a sewing needle. In this case, these stainless steel wires are cut to a predetermined length, tips thereof are sharpened into a conical or pyramid shape, and then a hole is made in the base end side using a drill or laser.

However, since the entirety from the tip to the base end is a fibrous structure, it is hard, and processing such as crimping to attach a suture thread to the sewing needle is difficult. Furthermore, the hole cracks even due to crimping, causing damage to the anatomy, which thereby reduces tension of the suture thread, making it easier to pull out. Accordingly, Japanese Patent Publication after examination (Kokoku) No. Hei 4-67978 proposes to heat the formed hole area using a burner flame, electrical resistance, or high-frequency induction to make it a structure without long crystal grains, soften it, and then carry out a crimping operation.

However, while the sewing needle described in Japanese Patent Publication after examination (Kokoku) No. Hei 4-67978 is formed with the hole included needle base having a granular crystalline structure without any directionality, the granular structure extends much further beyond the hole towards the needlepoint. Therefore, if a surgeon grips near the hole of the sewing needle when suturing, there is a problem that he/she grasps a flexible granular structure, resulting in a bent sewing needle. In this case, the needle should be gripped on the tip side, for example, a position approximately a third of the needle length from the needle base; however, depending upon suturing portions, there is a case where it is easier to suture by gripping closer to the hole, for example, a position approximately a quarter to a fifth of the needle length from the needle base. Needing to always grip on the tip side of the needle is stressful for the doctor.

Note that a tendency to grip the tip side of the needle at a position approximately three times the diameter of the sewing needle from the bottom of the hole is understood.

DISCLOSURE OF INVENTION

The present invention is devised through consideration of the aforementioned problems. An objective thereof is to provide a sewing needle impossible to bend even if gripped near the hole, and also provide a fabrication method for the same. For that purpose the sewing needle of the present invention is flexible near the hole so as to allow the hole periphery to be easily crimped while keeping a high hardness at a position slightly away from the hole towards the needlepoint side.

In order to attain the objective described above, the eyeless sewing needle, according to the present invention, includes a curved axial main body extending from a base end to a sharp needlepoint and is made of austenitic stainless steel with a fibrous structure in which a crystalline structure of the main body extending axially. It further includes an axial hole extending from the base end. It is characterized in that a periphery of the axial hole at the base end is heated to make the fibrous structure be a granular structure without directionality, and at least a part of a heat-affected zone made between the fibrous structure and the granular structure through the heating is within a range that is three times the diameter of the sewing needle and that extends from an effective base of the hole towards the needlepoint of the sewing needle.

Furthermore, a range approximately a quarter of the needle length away from the base end of the main body and further to the needlepoint does not include a granular crystalline structure but may include the heat-affected zone or a fibrous crystalline structure.

A fabrication method for an eyeless sewing needle including a curved axial main body extending from a base end to a sharp needlepoint and further including an axial hole extending from the base end is provided; wherein the main body has a crystalline structure made of austenitic stainless steel with a fibrous structure extending axially. This method is characterized by the steps of: heating the periphery of the axial hole at the base end to make the fibrous structure be a granular structure without directionality; and forming a heat-affected zone between the fibrous structure and the granular structure through the heating. At least a part of the heat-affected zone resides in the range that is three times the diameter of the sewing needle and that extends from an effective base of the hole towards the needlepoint of the sewing needle.

Moreover, the fabrication method for the eyeless sewing needle, according to present invention, is characterized in that a range approximately a quarter of the needle length away from the base end of the main body and further to the needlepoint does not include a granular crystalline structure but includes the heat-affected zone or a fibrous crystalline structure.

The eyeless sewing needle according to the present invention has a fibrous main body, and since it is hard, the base end is heated before or after making the hole in the base end surface to make a flexible granular structure, facilitating crimping and related operations. In addition, the needlepoint side remains a fibrous structure, securing strength required when suturing. While the base end is heated to be a granular structure, an area adjacent to the heated part is affected by the heat, turning into an intermediate state between the fibrous and the granular structure. This area is defined as a heat-affected zone, and the length of the granular structure is determined based on the position of this heat-affected zone. In other words, the further this heat-affected zone is positioned away from the effective base of the hole towards the needlepoint, the longer the flexible granular structure part on the base end side. If a surgeon grips near the hole of the sewing needle using a needle holder, it will easily bend. Therefore, as long as at least a part of the heat-affected zone is less than three times the needle diameter away from the effective base of the hole, the length of the flexible granular structure may be kept under three times the needle diameter away from the effective base of the hole towards the needlepoint. As a result, the sewing needle will not bend anymore, providing a convenient eyeless sewing needle, as long as it is not gripped with a needle holder very close to the needle base.

BEST MODE FOR CARRYING OUT THE INVENTION

An embodiment according to the present invention is described with reference to accompanying drawings forthwith.

Figure 1:
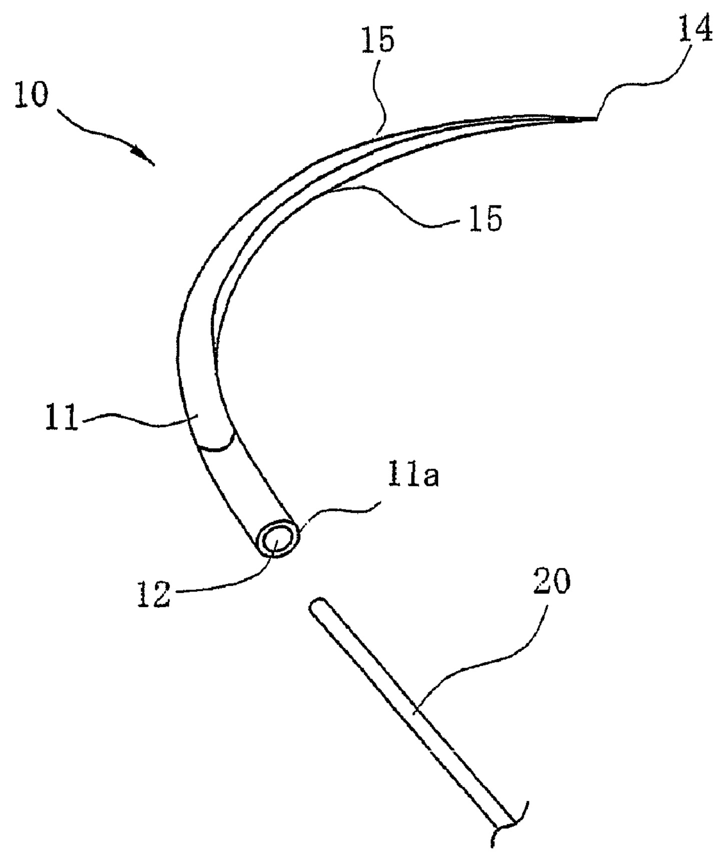
FIG. 1 is an oblique perspective of an eyeless sewing needle according to the present invention.

FIG. 1 is an oblique perspective of an eyeless sewing needle according to the present invention. As shown in this diagram, an eyeless sewing needle 10 is entirely made of austenitic stainless steel, a base end 11*a* is on an end of a main body 11, and an axial hole 12 is formed in this base end 11*a* which is cylindrically drilled along the longitudinal axis of the needle according to a processing method using a laser, an electron beam, electric discharge, a drill, or the like. Furthermore, a sharp needlepoint 14 is formed at the tip of the eyeless sewing needle 10, and a pyramid having a plurality of cutting blades 15 continuing from the needlepoint 14 is formed.

The eyeless sewing needle 10 may be a sewing needle with a sharpened edge (not shown in the drawing) in which the cross section of the cutting blades 15 as shown in FIG. 1 is formed into a polygon, a round needle (not shown in the drawing) without the cutting blades 15 having a cross section thereof formed in an approximate circle, or the like. These sewing needles are selected and used according to anatomy and region to be sutured.

Many types of suture thread 20 are provided in terms of different thicknesses and materials (nylon, silk, etc.) and/or different structures such as monofilament or multifilament. An appropriate type of suture thread is selected and used according to anatomy and region to be sutured. An end of the suture thread 20 is inserted in the axial hole 12, and the axial hole 12 is crushed and crimped by using a press machine, thus fixing the suture thread 20 to the base end of the eyeless sewing needle 10. The eyeless sewing needle 10 has an advantage in that a thread long enough for suturing is fastened from the start, and thus there is no need to pass a thread through a hole as with an eyed needle.

Figure 2:
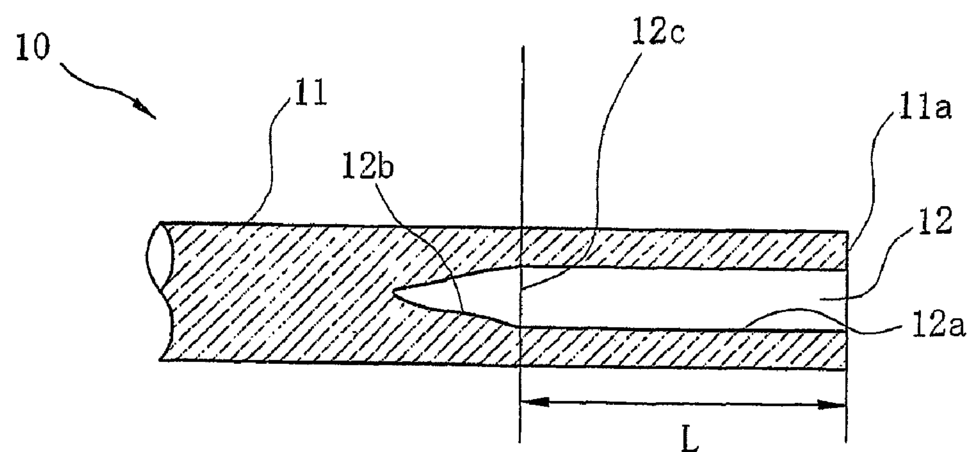
FIG. 2 is a magnified cross section of a base end of the eyeless sewing needle of FIG. 1.

FIG. 2 is a magnified cross section of a base end of the eyeless sewing needle 10 of FIG. 1. The base end 11*a* of the main body 11 has the axial hole 12 opened with a laser. The axial hole 12 has a part 12*a* somewhat wider than the diameter of the suture thread 20 and nearly straight so that the suture thread 20 can be inserted. A bottom part 12*b* of the axial hole 12 gradually narrows, finally ending in a dead end. The suture thread 20 can be inserted only in the nearly straight part 12*a*. A virtual surface formed at the boundary of the part 12*a* and the part 12*b* is called an effective base 12*c* of the axial hole 12, and distance L from the base end 11*a* of the axial hole 12 to the effective base 12*c* is called an effective depth. The diameter of the axial hole 12 is approximately 20 to 80% of diameter (diameter of the unprocessed main body 11) of the eyeless sewing needle 10, and the effective depth L is approximately 1.1 to 7 times the diameter.

Since the main body 11 of the eyeless sewing needle 10 is fibrous and hard, attaching a thread is not easy. Therefore, before or after making the axial hole 12, heating this base end part to be granular is necessary. Note that since making the axial hole 12 with a drill or the like causes work hardening at the inner surface of the axial hole 12, it is preferable to heat the base end part thereafter.

Figure 3:
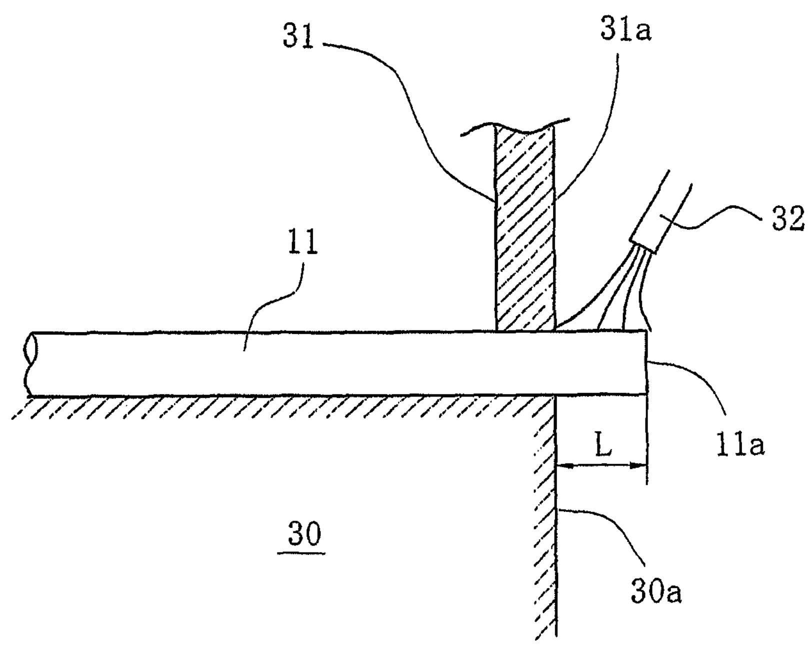
FIG. 3 is a diagram describing a method of heating the base end of a main body.

FIG. 3 is a diagram describing this heating method. The main body 11 of the eyeless sewing needle before the axial hole 12 is made includes the sharp needlepoint 14 with a plurality of the cutting blades 15 connected thereto.

This main body 11 is loaded onto a conveyer 30 and transported. At this time, the base end side of the main body 11 overhangs off from the conveyer 30 by just the effective depth L of the axial hole 12. An insulating board 31 and a burner 32 are provided at predetermined positions along the transporting path for the conveyer 30. A surface 31*a* on the outside of the insulating board 31 is the same as an outer surface 30*a* of the conveyer 30. The insulating board 31 may be a plaster board or one of various types of ceramics as long as it effectively shuts out heat from the burner 32.

Note that with this embodiment, while the overhanging length is set to L, this length is not limited thereto and should be determined based on conditions such as thickness of the eyeless sewing needle 10 and heat conditions of the burner 32.

When the eyeless sewing needle 10 that has been transported along the conveyer 30 reaches a predetermined position, it is held down from above by the insulating board 31, making a part of the base end side of the eyeless sewing needle 10 having a length "L" overhang. This length L part overhanging the outer side is heated to approximately 800° C.

by the flame of the burner 32. The heated eyeless sewing needle 10 is transported on the conveyer 30 away from the burner 32 and then cooled in the air. Through this heating and cooling, the base end in which the axial hole 12 is to be opened is changed and softened from having a fibrous structure to a granular structure. The axial hole 12 is then opened through laser processing or the like as in the conventional manner.

Figure 4:
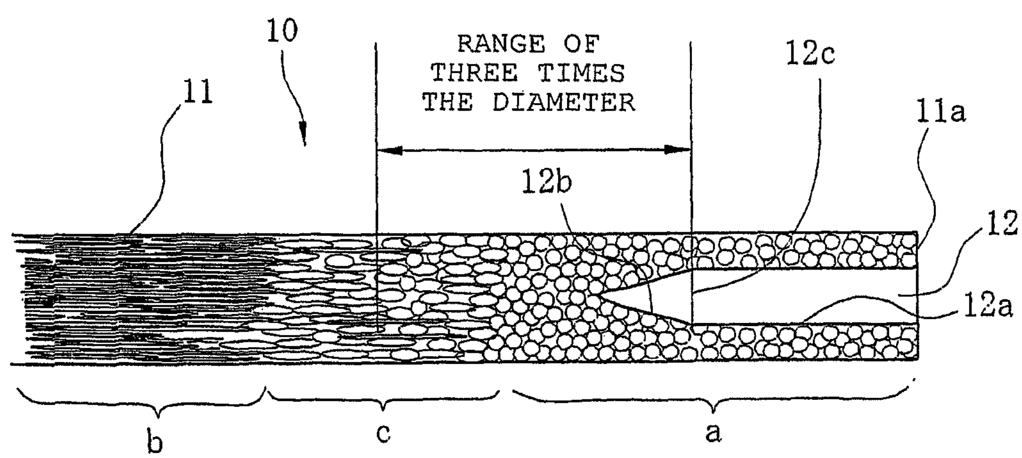
FIG. 4 is a diagram schematically showing a structure of a cross section after an axial hole is made.

FIG. 4 is a diagram schematically showing a structure of a cross section after the axial hole is made. The length L of the heated part is a depth represented by the effective base 12*c* of the axial hole, and a granular structure a exceeds the effective base 12*c* of the axial hole, reaching close to the bottom 12*b* of the axial hole 12. Furthermore, parts away from the axial hole 12 along the needle length are not affected by the heat, and thus a fibrous structure b remains the same, providing necessary hardness for the eyeless sewing needle 10. Moreover, a heat-affected zone c is formed between the granular structure a and the fibrous structure b. This heat-affected zone c is a chromium deficient region from which chromium carbide is finely precipitated, and is of poor corrosion resistance. Furthermore, the hardness of this heat-affected zone c is between that of the fibrous structure b and the granular structure a.

According to the present invention, the heat-affected zone c is positioned in a range approximately a quarter of the needle length away from the base end 11*a* of the main body 11, and a fibrous crystalline structure is formed in a portion extending from a quarter of the needle length from the base end 11*a* toward the needlepoint side of the sewing needle.

When the eyeless sewing needle 10 formed as described above is cut off at the center along the axis and the cross section is corroded by a means such as electrolytic etching, the heat-affected zone c is excessively etched due to the poor corrosion resistance, and only that heat-affected zone c turns black. This allows easy determination of the position and range of the heat-affected zone c.

Figure 5:
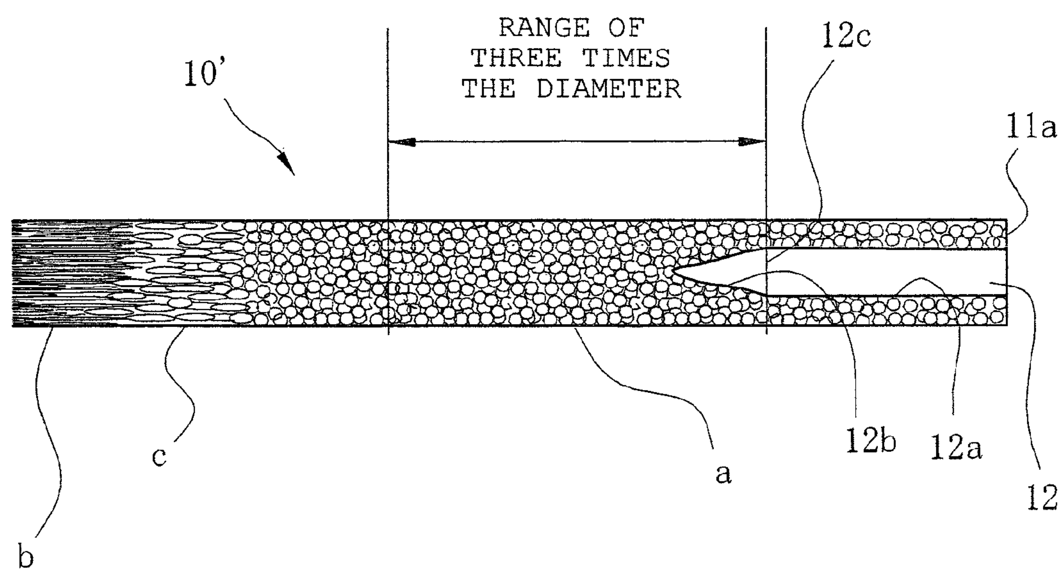
FIG. 5 is a diagram schematically showing a structure of a cross section of a conventional eyeless sewing needle.

FIG. 5 is a diagram schematically showing a structure of a cross section of a conventional eyeless sewing needle 10'. Since the base end is conventionally merely heated without any kind of control, quite a long part from the base end 11*a* is heated, the part having the granular structure a extends broadly towards the needlepoint from the effective base 12*c* of the axial hole 12, and the heat-affected zone c is then formed thereafter. Since the granular structure a is long, it is easy to grip the part having the granular structure a with a needle holder when suturing. However, when gripping the part having the granular structure a, there is a great risk that the eyeless sewing needle 10' will be bent.

As shown in FIG. 3, since the eyeless sewing needle 10 according to the present invention limits the heated part to the effective depth L of the axial hole by the use of the conveyer 30 and the insulating board 31, shortening the granular structure a is possible, as shown in FIG. 4. More specifically, the part of the granular structure a may be almost limited to the outer vicinity of the axial hole 12.

While axial lengths of the granular structure a and the heat-affected zone c fluctuate due to various contributing factors, as long as a portion of the heat-affected zone c is less than three times the needle diameter when measuring from the effective base 12*c* towards the needlepoint, the range in which the granular structure a is formed also mostly remains less than three times the needle diameter when measuring from the effective base 12*c* towards the needlepoint. Further towards the needlepoint, the heat-affected zone c and the fibrous structure b are formed which are hard in structure. As a result, use of the eyeless sewing needle 10 allows no gripping of the granular structure a, and prevents the eyeless sewing needle 10 being carelessly bent. It is thereby possible to provide a convenient eyeless sewing needle, even when gripping near the axial hole 12.

While the invention has been described with reference to particular example embodiments, further modifications and improvements which will occur to those skilled in the art, may be made within the purview of the appended claims, without departing from the scope of the invention in its broader aspect.

INDUSTRIAL APPLICABILITY

The present invention provides a convenient eyeless sewing needle which is impossible to bend even if gripped near the axial hole, and also provides a fabrication method for the same. For that purpose the sewing needle of the present invention is flexible near the axial hole so as to allow the hole periphery to be easily crimped while keeping a high hardness at a position slightly away from the axial hole towards the needlepoint side.

What is claimed is:

1. An eyeless sewing needle, which comprises a curved axial main body extending from a base end to a sharp needlepoint, and which is made of austenitic stainless steel with a fibrous structure in which a crystalline structure of the main body extending axially, and which further comprises an axial hole extending axially from the base end; wherein a periphery of the axial hole at the base end is heated to make the fibrous structure be a granular structure without directionality, and at least a part of a heat-affected zone made between the fibrous structure and the granular structure due to said heating is within a range that is three times the diameter of the sewing needle and that extends from an effective base of the axial hole towards the needlepoint of the sewing needle.

2. The eyeless sewing needle according to claim 1, wherein a range approximately a quarter of the needle length away from the base end of the main body and further to the needlepoint does not include a granular structure but the heat-affected zone or the fibrous structure.

* * * * *